(12) United States Patent
Pendergrass

(10) Patent No.: US 10,295,440 B2
(45) Date of Patent: May 21, 2019

(54) MECHANICAL PART-STREAM SAMPLER

(71) Applicant: Precision Samplers, Inc., South Charleston, WV (US)

(72) Inventor: Gregory T. Pendergrass, South Charleston, WV (US)

(73) Assignee: PRECISION SAMPLERS, INC., South Charleston, WV (US)

( * ) Notice: Subject to any disclaimer, the term of this patent is extended or adjusted under 35 U.S.C. 154(b) by 358 days.

(21) Appl. No.: 14/990,397

(22) Filed: Jan. 7, 2016

(65) Prior Publication Data

US 2016/0266014 A1 Sep. 15, 2016

Related U.S. Application Data

(60) Provisional application No. 62/100,778, filed on Jan. 7, 2015.

(51) Int. Cl.
| | |
|---|---|
| *G01N 1/20* | (2006.01) |
| *G01N 1/04* | (2006.01) |
| *B26D 7/32* | (2006.01) |
| *B26D 5/38* | (2006.01) |
| *B26D 5/00* | (2006.01) |
| *B26D 1/12* | (2006.01) |
| *B26D 1/44* | (2006.01) |
| *B26D 7/18* | (2006.01) |
| *B26D 7/26* | (2006.01) |

(52) U.S. Cl.
CPC ............. *G01N 1/04* (2013.01); *B26D 1/12* (2013.01); *B26D 1/44* (2013.01); *B26D 5/005* (2013.01); *B26D 5/38* (2013.01); *B26D 7/18* (2013.01); *B26D 7/26* (2013.01); *B26D 7/32* (2013.01)

(58) Field of Classification Search
CPC .............................................. G01N 2001/2028
See application file for complete search history.

(56) References Cited

U.S. PATENT DOCUMENTS

| | | | | |
|---|---|---|---|---|
| 4,133,210 A | * | 1/1979 | Jaeger | G01N 1/20 73/863.91 |
| 2002/0000131 A1 | * | 1/2002 | Long | G01N 1/20 73/863.56 |
| 2009/0205446 A1 | * | 8/2009 | Lyman | G01N 1/08 73/863.91 |
| 2011/0011702 A1 | * | 1/2011 | Jansson | G01N 1/04 198/637 |

\* cited by examiner

*Primary Examiner* — Robert R Raevis
(74) *Attorney, Agent, or Firm* — Birch, Stewart, Kolasch & Birch, LLP

(57) ABSTRACT

A mechanical part-stream sampler includes a housing positionable over a conveyor belt from which material is to be sampled. The housing encases one or more cutter arms and adjustable cutters. The cutter arms rotate 360 degrees such that the cutters extract a sample of material from the conveyor belt and deposit the sample in a discharge chute in the housing for later analysis. A programmable logic controller and human machine interface screen can be used to operate the sampler and to control the timing and speed of the cutter arms.

8 Claims, 3 Drawing Sheets

MECHANICAL PART-STREAM SAMPLER

CROSS REFERENCE TO RELATED APPLICATIONS

This application claims the benefit of U.S. provisional application No. 62/100,778, filed Jan. 7, 2015, the contents of which are incorporated herein by reference.

FIELD OF INVENTION

This application relates to product sampling, and, more specifically, to a method and apparatus for sampling products having different particle sizes being transported on a conveyor belt.

BACKGROUND

The export coal terminals in the US have a very high throughput and utilize very large conveyor belts for loading vessels. These operations are typically operated 24/7 and sampling must be continuous as well since the product is highly sensitive to changing coal qualities. In the event the primary sampling system becomes inoperable, the traditional acceptable method of sampling has been to temporarily sample manually.

Manual sampling basically requires a man with a shovel in hand being given the task of collecting shovels of coal from a moving conveyor. This means of sampling has always been a dangerous task but has become especially so since the larger operations are moving to even larger conveyors and higher feed rates.

Due to the fact that the chemical characteristics of commercial interest are often distributed unequally in the different sized particles in a consignment—and that solid bulk cargos segregate by size when handled—the capturing of the particle size distribution of the consignment in the sample increments is critical to collecting an unbiased sample.

The fundamental rule of sampling a bulk cargo is that each particle of equal mass in a consignment must have an equal chance of being selected in the sample. However, this requirement is not met by all ASTM sampling methods.

According to ASTM Standard D 2234, there are four Conditions (or Types) of Sampling:
  Condition A—Stopped Belt Sampling
  Condition B—Full Stream Sampling
  Condition C—Part Stream Sampling
  Condition D—Stationary Sampling (Stockpiles, barges, railcars, etc.)

Conditions A and B are Probability Sampling—because each particle in the consignment has a non-zero chance of being selected for the sample. When executed properly, these can overcome particle size segregation, or moisture migration, in the consignment.

Conditions C and D are considered to be Non-Probability Sampling—because some particles in the consignment have zero chance of being selected. Even when executed properly, these cannot always overcome particle size segregation or moisture migration. For this reason, Non-Probability Sampling is often called "Judgment sampling" (as in human judgment).

What is needed in the industry is a mechanical sampling system that can be used safely and effectively while the permanent sampling system is unavailable for use temporarily.

SUMMARY

The present invention solves the foregoing problems by providing a mechanical part-stream sampler with cutter arms and adjustable cutters designed to extract a material sample from a conveyor belt while moving parallel to the conveyor belt.

The mechanical part-stream sampler (MPS) of the present invention complies with ASTM Standard D 6609—Standard Guide to the Part-Stream Sampling of Coal and provides a safe back-up sampling method whenever a mechanical sampling system is out of service. The industry-accepted alternative method has long been to collect manual samples from a moving conveyor utilizing human labor. In recent years, however, conveyor belts have become larger and faster. The apparatus of the present invention is an effective and safe alternative to manual sampling.

The MPS can be fitted to most existing conveyor structures and is ideal for collecting part-stream samples where no full-stream mechanical sampling system is installed. This can be the case at terminals with low throughput tonnage or infrequent sampling requirements. While originally developed for coal, this device can be used for any bulk solid transported by a conveyor belt.

The MPS is not intended to replace mechanical sampling because full stream mechanical sampling is Condition B, which is widely used because it is Probability Sampling. The MPS is Condition C sampling and therefore is Non-Probability Sampling.

A first aspect of the invention is a mechanical part-stream sampler including one or more cutters for extracting a sample of material from a moving conveyor belt; a cutter arm connected to each of the one or more cutters; a drive assembly for rotating the cutter arm and cutter at a desired speed relative to the convnor belt from which the sample is to be extracted; a cutter shaft for connecting the drive assembly to the cutter arm; a cutter shaft bearing to secure the cutter shaft in place and to guide the cutter shaft during rotation; a housing assembly having a discharge chute to transfer extracted product samples from the cutter to a save sample container; and a discharge chute throat skirt around the discharge chute opening for preventing extraneous material from entering the discharge chute; an exit skirt assembly for directing misplaced material back onto the conveyor belt as it passes through the housing assembly; and control means for operating the apparatus.

A second aspect of the invention is a mechanical part-stream sampler including a housing assembly positonable over a conveyor belt from which a sample of material is to be extracted; a cutter arm secured to the housing and positioned above the conveyor; and a cutter connected to an end of the cutter arm, wherein the cutter extracts a sample of material from the conveyor when the cutter arm rotates.

A feature of the invention is that it has two alternating cutters to reach both sides of the conveyor belt.

Another feature of the invention is that the cutters are designed to reach deeper into a material to be sampled than is possible by a person with a shovel.

Another feature of the invention is that the cutters operate in the same direction of the material flow on the conveyor belt.

Another feature of the invention is that that the frequency of sampling is programmable, based on the lot size and flow rate calculations.

Another feature of the invention is that it has a small footprint on the conveyor belts.

DETAILED DESCRIPTION

Figure 1:
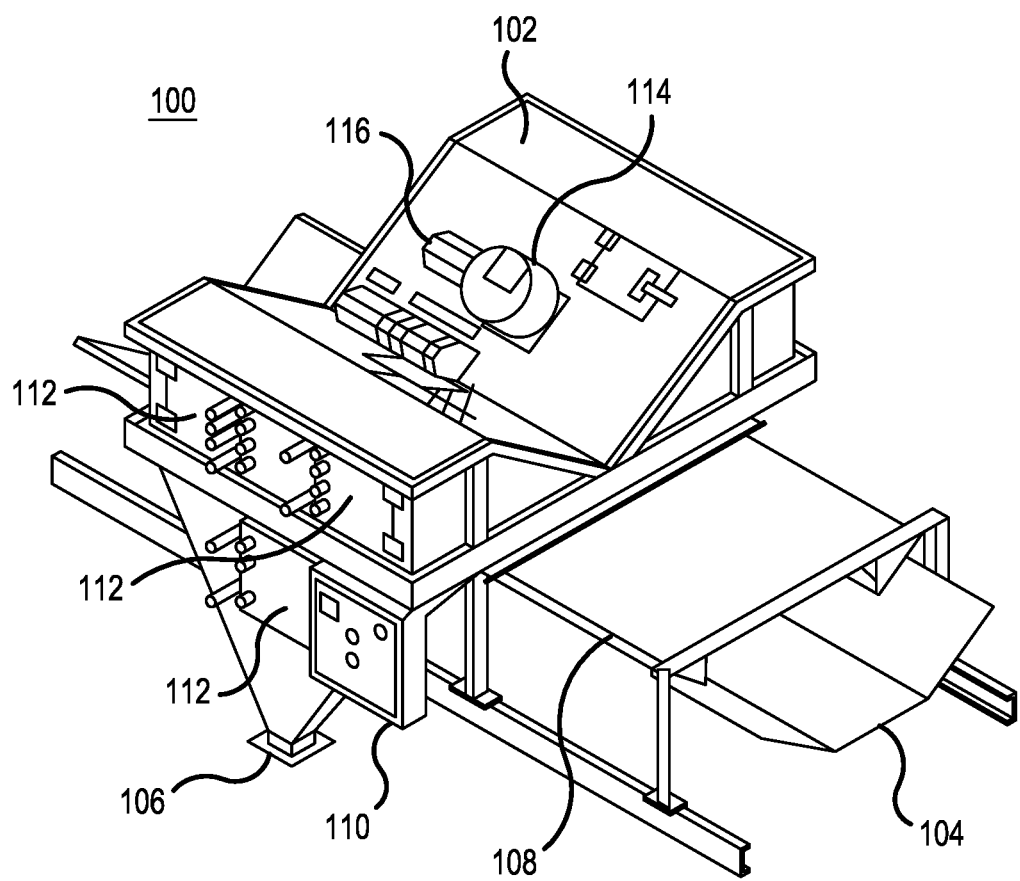
FIG. 1 is a perspective view of the exterior of an embodiment of the mechanical part-stream sampler (MPS) of the present invention.

Referring generally to FIG. 1, there is shown one of many possible embodiments of a mechanical part-stream sampler (MPS) 100 of the present invention. The MPS 100 can collect material sample increments from a moving conveyor belt by utilizing single or dual rotary arms, which are referred to herein as cutter arms. In a preferred embodiment, dual cutter arms are used to capture material from both sides of the conveyor belt, which minimizes the effects of particle size segregation and allows for better sampling of mixed qualities. As discussed in more detail below, the speed and frequency of the cutter arms can be controlled by a programmable logic control module (PLC) and adjusted through a simple human machine interface (HMI) screen.

The cutter arms optionally but preferably can rotate 360 degrees in the same direction of the material flow. The speed of the rotation is designed to be slightly faster than the speed of the conveyor belt to mimic collecting a scoop from a stationary conveyor and to minimize stress on the motor drives. The sample scoops, also referred to as "cutters," can be custom designed for the specific material being sampled, and can be adjusted in the field to an effective but safe distance from the conveyor belt. Sample increments can be deposited by centripetal force into a discharge chute on the same side as the cutter arm. The sample increments can be captured in sealed containers or bags until they can be further processed.

The MPS 100 includes an exterior housing assembly 102 (housing) that can be positioned over a conveyor belt 104 from which samples of material are to be extracted. The housing 102 also encases the cutter arms and cutters. The housing 102 can include a discharge chute 106 to transfer extracted sample material to a save sample container. Optionally but preferably, the housing 102 has two discharge chutes 106, one for each cutter arm inside the housing 102. Each discharge chute 106 can be fabricated from 3/16" thick 304 stainless steel and includes hinged cleanout access doors and gasketed flanges. The opening leading into the discharge chute 106 can be protected with throat skirting 250 to prevent extraneous material from entering the discharge chute 106. Examples of such extraneous material can include that which is generated from the displacement of material resulting from the action of the cutter as well as misplaced material on the main conveyor belt from its loading. An exit skirt 108 can be positioned over the conveyor belt 104 to contain any misplaced material and to divert it back onto the conveyor belt 104 as it passes through the housing 102. The exit skirt 108 can be fully adjustable and can be fabricated from 3/16" 304 stainless steel.

The MPS 100 includes control means for operating the cutter arms and cutters, which can be rotated at different time increments and at various speeds. The control means can include a control panel 110, e.g., a NEMA 4× stainless steel enclosure, that encloses a main power disconnect, PLC Control Module, and human machine interface (HMI), e.g., Allen Bradley or equivalent. A cutter position sensor optionally but preferably is included and is protected by the cutter position sensor housing 114.

The MPS 100 can include a discharge chute vibrator that is particularly helpful when the material being sampled is of high moisture content and it is difficult to maintain flow within the chute. A plugged chute indicator, which is used to detect when the discharge chute gets plugged or otherwise obstructed, can included. The plugged chute indicator preferably is in communication with the discharge chute vibrator, and caused the discharge chute vibrator to vibrate automatically when the discharge chute is plugged. A product-on-belt sensor can be included to assure that the MPS 100 attempts to extract sample increments only when material is being conveyed on the conveyor belt 104. One or more access doors 112 can be positioned on the outside of the housing 102 adjacent or otherwise near the control panel 110 to permit access to the inside of the housing 102 and the discharge chute 106.

The MPS 100 includes a drive assembly 116 for rotating the cutter arm and cutter at a desired speed relative to the conveyor belt from which the sample is to be extracted. The size of the gearing and input horsepower of the drive assembly 116 both are application contingent. For example: an MPS 100 designed for a 48" wide main conveyor moving 1500 tons per hour has a lower horsepower and speed requirement than a 96" wide main conveyor moving 7000 tons per hour. The drive assembly 116 can be secured to the housing 102 by a heavy duty mounting collar 302.

Figure 2:
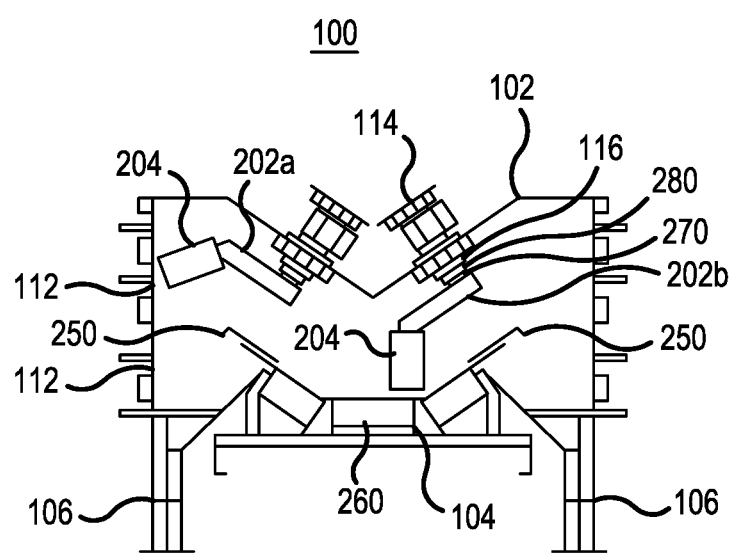
FIG. 2 is a plan view of an embodiment of the MPS of the housing of an embodiment of the MPS.
Figure 3:
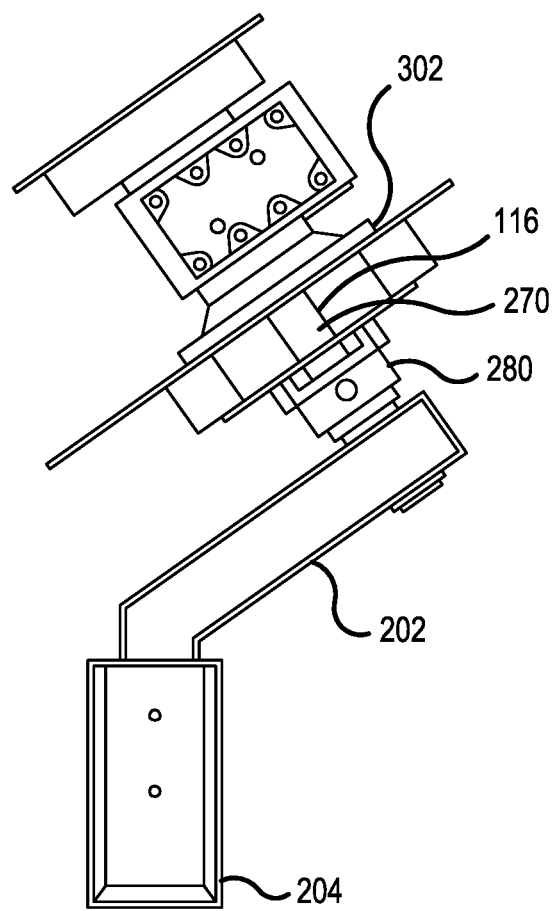
FIG. 3 is a plan view of an embodiment of the cutter and drive assembly of the MPS.

Referring to FIG. 2, the interior of the housing 102 can be seen relative to the conveyor belt 104 and conveyor belt supporting idler 260. The MPS 100 optionally but preferably includes two cutter arms 202. A first cutter arm 202a is shown in a "parked" or inactive position, and a second cutter arm 202b in a "sample" or active position. Each cutter arm 202 is a heavy duty mechanical arm that connects the drive assembly 116 output shaft to the cutter 204. The cutter arms 202 are fabricated from 3/16" thick 304 stainless steel structural tubing, and each is designed to extract the sample increment parallel to the flow of material on the conveyor belt 104 and continue to a stopping point, which allows the entire sample increment to be discharged in its entirety into the sample save discharge chute 106. For each drive assembly 116, a heavy duty drive shaft 270 is utilized to connect the drive assembly 116 to the cutter arm 202. The drive shaft 270 is machined from 1045 TP shaft material. The diameter of the draft shaft 270 is specifically designed for each application and is contingent on the output horsepower of the drive assembly 116. A cutter shaft bearing 280, preferably a piloted flange mounted bearing, is utilized to hold the drive shaft 270 in place and to guide it while rotating. The size of the cutter shaft bearing 280 is also contingent on the application.

Each cutter 204 is a heavy duty adjustable sample scoop fabricated from 1/4" thick 304 stainless steel. The cutters 204 are adjustable in 1/2" increments to allow the cutters 204 to be adjusted relative to the conveyor belt 104 and depth of material on the conveyor belt 104 to be sampled. The geometric shape of the cutter 204 is designed to collect a complete sample increment and prevent loss throughout its operation in regard to size degradation.

In operation, the MPS 100 is positioned with the housing 102 over a conveyor belt 104 from which materials are to be sampled. Depending on the sampling criteria, e.g., material characteristics, flow rate, etc., the sampling frequency and the rotational speed of the cutter arms 202 and cutters 204 can be programmed using the control panel 110.

At the appropriate time, the cutter arms 202 alternately rotate 360 degrees such that the cutter 204, moving parallel to the moving conveyor, extracts a sample of the material being conveyed. The drive assembly 116 rotates the cutter arm 202 and cutter 204 at a desired speed relative to the conveyor belt 104 from which the sample is to be extracted.

The size of the gearing and input horsepower of the drive assembly 116 both are application contingent. For example: an MPS 100 designed for a 48" wide main conveyor moving 1500 tons per hour has a lower horsepower and speed requirement than a 96" wide main conveyor moving 7000 tons per hour. The drive assembly 116 is be secured to the housing 102 by a heavy duty mounting collar 302.

Sample increments are deposited by centripetal force into a discharge chute 106 on the same side as the cutter arm 202. The sample increments can be captured in sealed containers or bags until they can be further processed. The opening leading into the discharge chute 106 is protected with throat skirting 250 to prevent extraneous material from entering the discharge chute 106. An exit skirt 108 also is positioned over the conveyor belt 104 to contain any misplaced material and to divert it back onto the conveyor belt 104 as it passes through the housing 102. The exit skirt 108 is fully adjustable and can be fabricated from 3/16" 304 stainless steel.

CONCLUSION

While various embodiments of the present invention have been described above, it should be understood that they have been presented by way of example only, and not limitation. It will be understood by those skilled in the art that various changes in form and details may be made therein without departing from the spirit and scope of the invention. Thus, the breadth and scope of the invention should not be limited by any of the above-described exemplary embodiments.

What is claimed is:

1. An apparatus, comprising:
   a housing assembly positioned over a conveyor belt from which a sample of material is to be extracted;
   a first cutter arm secured to a first side of the housing assembly and positioned above a first side of the conveyor;
   a second cutter arm secured to a second side of the housing assembly and positioned above a second side of the conveyor;
   a first cutter connected to an end of the first cutter arm, wherein the first cutter is generally rectangular with a bottom surface and four walls extending vertically from the bottom surface to create an opening opposite the bottom surface, and further wherein the first cutter arm and first cutter rotate 360 degrees such that the first cutter is moving in the same direction as the conveyor belt as the first cutter extracts a sample of material from the first side of the conveyor belt when the first cutter arm rotates; and
   a second cutter connected to an end of the second cutter arm, wherein the second cutter is generally rectangular with a bottom surface and four walls extending vertically from the bottom surface to create an opening opposite the bottom surface, and further wherein the second cutter arm and cutter rotate 360 degrees such that the second cutter is moving in the same direction as the conveyor belt as the second cutter extracts a sample of material from the second side of the conveyor belt when the second cutter arm rotates.

2. The apparatus of claim 1, further comprising:
   a first drive assembly for rotating the first cutter arm and first cutter at a desired speed relative to the conveyor belt from which the sample is to be extracted; and
   a first cutter shaft for connecting the first drive assembly to the first cutter arm.

3. The apparatus of claim 1, further comprising an exit skirt assembly secured underneath the housing assembly and positioned above and around a top surface of the conveyor belt for preventing material on the conveyor belt from falling off the conveyor belt as it passes through the housing assembly.

4. The apparatus of claim 1, further comprising control means for operating the apparatus.

5. The apparatus of claim 1, wherein the housing assembly comprises a first discharge chute to transfer extracted product samples from the first cutter to a save sample container.

6. The apparatus of claim 5, wherein the housing assembly further comprises a discharge chute throat skirt around the first discharge chute opening for preventing extraneous material from entering the first discharge chute.

7. The apparatus of claim 5, wherein the housing assembly comprises a second discharge chute to transfer extracted product samples from the second cutter to a save sample container.

8. The apparatus of claim 7, wherein the housing assembly further comprises a second discharge chute throat skirt around the second discharge chute opening for preventing extraneous material from entering the second discharge chute.

* * * * *